United States Patent
Gouma et al.

(10) Patent No.: US 8,955,367 B2
(45) Date of Patent: Feb. 17, 2015

(54) GAS SENSOR WITH COMPENSATIONS FOR BASELINE VARIATIONS

(75) Inventors: Pelagia-Irene Gouma, Port Jefferson, NY (US); Milutin Stanacevic, Forest Hills, NY (US)

(73) Assignee: The Research Foundation of University of New York, Albany, NY (US)

( * ) Notice: Subject to any disclaimer, the term of this patent is extended or adjusted under 35 U.S.C. 154(b) by 195 days.

(21) Appl. No.: 13/511,868

(22) PCT Filed: Dec. 2, 2010

(86) PCT No.: PCT/US2010/058744
§ 371 (c)(1),
(2), (4) Date: Sep. 28, 2012

(87) PCT Pub. No.: WO2011/068976
PCT Pub. Date: Jun. 9, 2011

(65) Prior Publication Data
US 2013/0125617 A1    May 23, 2013

Related U.S. Application Data

(60) Provisional application No. 61/265,979, filed on Dec. 2, 2009.

(51) Int. Cl.
*G01N 33/497* (2006.01)
*G01N 27/04* (2006.01)
(Continued)

(52) U.S. Cl.
CPC ............ *G01N 33/497* (2013.01); *G01N 27/122* (2013.01); *G01N 33/0006* (2013.01); *G01N 27/12* (2013.01)
USPC .......................................................... 73/23.3

(58) Field of Classification Search
CPC ............ G01N 21/274; G01N 21/3504; G01N 15/1459; G01N 15/147; G01N 27/00; G01N 27/028; G01N 33/0006; G01N 33/497; G01N 27/122

USPC .......................................................... 73/23.3
See application file for complete search history.

(56) References Cited

U.S. PATENT DOCUMENTS 3,714,421 A * 1/1973 Josias et al. ..................... 73/23.4
3,786,675 A * 1/1974 Delatorre et al. ............ 73/25.03
(Continued)

FOREIGN PATENT DOCUMENTS

| CN | 1623090 | 6/2005 |
|---|---|---|
| CN | 1902485 | 1/2007 |

(Continued)

OTHER PUBLICATIONS

Wang, L. and Yun, X. and Stanacevic, M. and Gouma, P. I., "An Acetone Nanosensor for Non-invasive Diabetes Detection," AIP Conference Proceedings, 1137, pp. 206-208 (Apr. 15-17, 2009).*

(Continued)

*Primary Examiner* — Lisa Caputo
*Assistant Examiner* — Punam Roy
(74) *Attorney, Agent, or Firm* — Preti Flaherty Beliveau & Pachios LLP

(57) ABSTRACT

Reliable, fast and inexpensive breath gas detector systems for medical diagnostics, including personal, handheld monitoring devices for a variety of diseases and conditions, including, for example, asthma, diabetes, blood cholesterol, and lung cancer. A sensor device (100) for detecting gases includes a sensing element (109) having an electrical resistance that changes in the presence of a target gas; a readout circuit, electrically coupled to the sensing element due to the presence of the target gas and converts the measurement to a digital signal; and a feedback loop (203) from a digital unit (205) to the readout circuit to compensate for variations in a baseline resistance of the sensing element.

34 Claims, 2 Drawing Sheets

(51) Int. Cl.
*G01N 27/12* (2006.01)
*G01N 33/00* (2006.01)

(56) References Cited

U.S. PATENT DOCUMENTS

| | | | | |
|---|---|---|---|---|
| 4,713,558 | A * | 12/1987 | Russell et al. | 327/307 |
| 5,448,905 | A * | 9/1995 | Stetter et al. | 73/31.05 |
| 5,656,813 | A * | 8/1997 | Moore et al. | 250/330 |
| 5,767,683 | A * | 6/1998 | Stearns et al. | 73/28.02 |
| 6,047,031 | A * | 4/2000 | Allott et al. | 375/317 |
| 6,085,576 | A * | 7/2000 | Sunshine et al. | 73/23.2 |
| 7,017,389 | B2 * | 3/2006 | Gouma | 73/31.05 |
| 7,460,958 | B2 * | 12/2008 | Walsh et al. | 702/24 |
| 7,763,208 | B2 * | 7/2010 | Steichen et al. | 422/88 |
| 2005/0142030 | A1 | 6/2005 | Kim et al. | |
| 2006/0199271 | A1 * | 9/2006 | Lian et al. | 436/155 |
| 2008/0077037 | A1 * | 3/2008 | Gouma et al. | 73/23.3 |
| 2009/0126454 | A1 | 5/2009 | Pratt et al. | |
| 2011/0277538 | A1 * | 11/2011 | Haick | 73/23.3 |
| 2012/0326092 | A1 * | 12/2012 | Haick et al. | 252/408.1 |

FOREIGN PATENT DOCUMENTS

| | | |
|---|---|---|
| CN | 101073007 | 11/2007 |
| CN | 101165480 | 4/2008 |

OTHER PUBLICATIONS

Grassi, Marco, Piero Malcovati, and Andrea Baschirotto. "A 160 dB equivalent dynamic range auto-scaling interface for resistive gas sensors arrays." Solid-State Circuits, IEEE Journal of 42.3 (2007) pp. 518-528.*

Liberali, V., P. Malcovati, and F. Maloberti. "Sigma-delta modulation and bit-stream processing for sensor interfaces." Proceedings of Italian Conference on Sensors and Microsystems. 1996. pp. 1-5.*

Hagleitner, Christoph. "Multi-Sensor Interfaces." Analog Circuit Design. Springer US, 2004. 43-64.* de Lacy Costello, B. P. J., et al. "The characteristics of novel low-cost sensors for volatile biomarker detection." Journal of breath research 2 (Sep. 8, 2008) 037017.*

Ding J et al., "Redundant Sensor Calibration Monitoring Using Independent Component Analysis and Principal Component Analysis", Real Time Systems, Kluwer Academic Publishers, Dordecht, NL, vol. 27, Jan. 1, 2004, pp. 27-47.*

McKennoch, S. "Auto-Zeroing Baseline Compensation for Chemical Sensor Signal Extraction," Diss. University of Washington, 2002.*

Chueh, H.-T. and Hatfield, J. V., "A real-time acquisition system for a hand-held electronic nose (H2EN)," Sensors and Actuators B 83 (2002) pp. 262-269.*

Pravdova, V., Pravda, M., Guilbault, G. G., "Role of chemometrics for electrochemical sensors," Analytical Letters, vol. 35, No. 15, (2002) pp. 2389-2419.*

Zhang, J., Zhou, J., Mason, A., "Highly adaptive transducer interface circuit for multiparameter microsystems," IEEE Transactions on Circuits and Systems—I: Regular Papers, vol. 54, No. 1 (Jan. 2007) pp. 167-178.*

Lin, Y., Gouma, P., Stanacevic, M., "A low-power wide dynamic-range readout IC for breath analyzer system," Circuits and Systems (ISCAS), 2013 IEEE International Symposium on. IEEE (2013) pp. 1821-1824.*

Gouma et al, "Selective nanoprobes for 'signalling gases,'" Institute of Physics Publishing, Nanotechnology 17 (2006) S48-S53.

Kermit et al., "Independent component analysis applied on gas sensor array measurement data," IEEE Sensors Journal, vol. 3, No. 2, Apr. 2003.

* cited by examiner

GAS SENSOR WITH COMPENSATIONS FOR BASELINE VARIATIONS

CROSS REFERENCE TO RELATED APPLICATION

This application claims the benefit of U.S. Provisional Application No. 61/265,979, filed Dec. 2, 2009, the entire contents of which are incorporated herein by reference.

STATEMENT REGARDING FEDERALLY SPONSORED RESEARCH OR DEVELOPMENT

This invention was made with government support under grant number DMR0304169 awarded by the National Science Foundation. The government has certain rights in the invention.

BACKGROUND

Medical studies reported recently have associated certain gaseous constituents of the human breath with specific types of diseases, and have addressed the importance of diet, dental pathology, smoking, etc, on determining the physiological levels of the marker concentrations in exhaled breath. Inflammation and oxidative stress in the lungs can be monitored by measuring the changes in the concentration of the following gases: NO (which has been widely studied as a bio-marker), and related products NO2-(nitrite); NO3-(nitrite); exhaled CO (also a marker for cardiovascular diseases, diabetes, nephritis, bilirubin production); exhaled hydrocarbons of low molecular mass, such as ethane, n-pentane; ethylene, isoprene (hydrocarbon affected by diet with is a marker for blood cholesterol levels); acetone, formaldehyde; ethanol; hydrogen sulfide, carbonyl sulfides, and ammonia/amines. For example, measurements of exhaled ammonia may differentiate between viral and bacterial infections in lung diseases to justify use of antibiotics.

Various sensors have been developed measuring these metabolites. Examples are described in, for example, U.S. Pat. No. 7,017,389, the entire contents of which are incorporated herein by reference. There is a continuing need for improvements in diagnostic tool breath analyzers that can provide, for example, a first detection device for fast and early diagnosis of medical conditions.

SUMMARY

The present invention is directed to reliable, fast and inexpensive breath gas detector systems for medical diagnostics, including, in some embodiments, personal monitoring devices for a variety of diseases and conditions, including, for example, asthma, diabetes, blood cholesterol, and lung cancer. The design of integrated microsystems and system-on-a-chip solutions combined with advances in sensor technologies allow for significant miniaturization of sensor devices for gas concentration sensing and integration into handheld devices.

In one embodiment, a sensor for detecting gases comprises a sensing element having an electrical resistance that changes in the presence of a target gas; a readout circuit, electrically coupled to the sensing element, that measures a change in the resistance of the sensing element due to the presence of the target gas and converts the measurement to a digital signal; and a feedback loop from a digital unit to the readout circuit to compensate for variations in a baseline resistance of the sensing element.

In certain embodiments, the gas sensor is incorporated in a handheld unit, having a suitable power source, such as a battery, and a display device, such as an LED indicator, included in the unit. One or more heating elements and temperature sensors can be provided to enable precise temperature control within the gas sensor. The sensor device can comprise an array of sensing elements, with a multi-channel integrated readout circuit.

According to one embodiment, the readout circuit comprises an A/D converter that converts the measurement of the change in the resistance of the sensing element to a digital signal. The A/D converter can comprise, for example, a first-order single-bit delta-sigma modulator device with a digitally configurable oversampling ratio for controlling the conversion scale. In certain embodiments, the resistance recording system has a resolution of 16-bits and a bandwidth of up to 1 kHz.

In some embodiments, the gas sensor is configured to maintain a constant current through the sensing element and measures a change in voltage due to the change in resistance. Alternatively, the sensor maintains the sensing element biased at a constant voltage and measures a change in current due the change in resistance.

The feedback loop can, in some embodiments, utilize an independent component analysis (ICA) based signal processing apparatus for compensating for variations in the baseline resistance of the sensing element. A current D/A converter converts a digital signal from the digital unit to a bias current that is provided to the sensing element. The current D/A converter can comprise, for example, a multi-bit (e.g. 10 bit) segmented D/A converter having at least one binary weighted bit and at least one unary weighted bit. The least significant bit(s) can be binary weighted and the most significant bit(s) can be unary weighted to provide a suitable compromise between complexity and monotonicity.

The present invention further relates to methods of detecting gases using a gas sensor as described above, including methods of detecting breath gases for medical diagnostics. Additional details can be found in "An Acetone Nanosensor For Non-invasive Diabetes detection," by Wang et al. in the Proceedings of the 13$^{th}$ International Symposium of the American Institute for Physics of May 23, 2009, Vol. 113 (Issue 1), pages 206-208, the entire contents of which is incorporated herein by reference.

In some embodiments, the present invention is a personal breath analyzer for fast and early diagnosis. The diagnostic tool breath analyzer provides a first detection device which can direct more complex diagnostic tools where to focus attention. The personal breath analyzer can also be of great significance in the case of emergency diagnostic, where due to chemical or biological threat, the time of detection and priority of possible victims can be of essence in response to such threat. The present breath analyzer tool is also very useful in low-resource settings, for health monitoring of underprivileged populations, etc.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

This application claims the benefit of U.S. Provisional Application No. 61/265,979, filed Dec. 2, 2009, the entire contents of which are incorporated herein by reference.

The present invention includes in a preferred embodiment a low-complexity low-power solution for the measurement of gas concentrations from a handheld gas measurement unit. The sensor behaves electronically as a resistance, and therefore a specialized multi-channel instrumentation is required to obtain readouts. VLSI technology offers several advantages for implementation of a highly integrated readout circuitry, including high sensitivity, small feature size, low noise, low power and modularity. The resistance is first converted to a voltage measurement, and the voltage signal is digitized. The input voltage is digitized using an A/D converter design that employs the first-order single-bit delta-sigma modulator architecture with a digitally configurable oversampling ratio for controlling the conversion scale.

Figure 1:
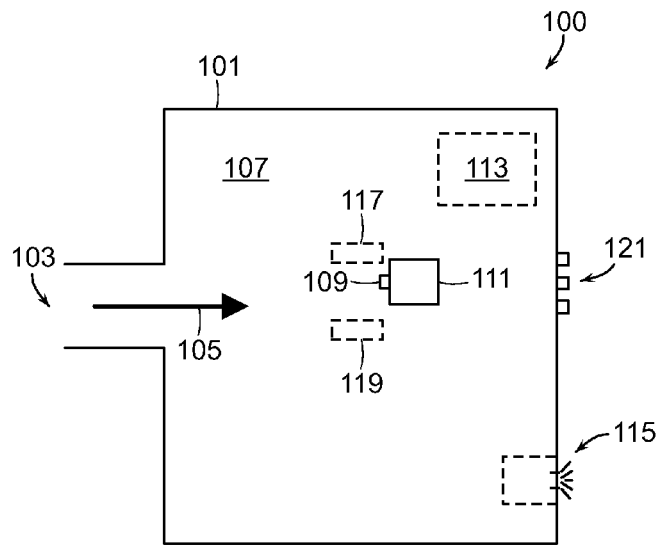
FIG. 1 is a schematic illustration of a handheld diagnostic breath analyzer according to one embodiment.

A handheld diagnostic breath analyzer device 100 according to one embodiment is illustrated schematically in FIG. 1. The device 100 includes a housing 101 having an opening 103 for receiving a gas 105 to be analyzed. In a diagnostic application, a patient exhales breath gas 105 into the opening 103. The breath gas 105 enters a chamber 107 where the gas 105 interacts with one or more sensor elements 109. The sensor elements 109 have a property that changes based on the chemical composition of the gas 105 with which it interacts. In one embodiment, the electrical resistance of the sensor elements 109 changes in response to the presence or absence of particular constituents of the gas 105. Examples of suitable sensor elements 109 are described in, for example, U.S. Pat. No. 7,017,389, which has been incorporated herein by reference. An integrated circuit device 111 is electrically coupled to the sensor element 109. The integrated circuit device 111 is configured to read out the change in resistance in the sensor element 109 and convert this change to a suitable electronic signal, such as a digital signal. In some embodiments, the device 100 includes an array of sensor elements 109, and the integrated circuit device 111 enables multi-channel read-out and signal processing. The sensor elements 109 can be integrated on the circuit device 111.

The analyzer device 100 of FIG. 1 further includes a power source 113, such as a battery, and a display device 115. The display device 115 can include, for example, one or more LED indicators that can be configured to indicate the presence or absence of a particular target substance in the breath gas 105. The display device 115 can be configured to indicate when a threshold amount of one or more substances are detected in the breath gas 105, for example. The display can be configured to display a diagnosis of a particular medical condition associated with the detected chemical constituent(s) of the breath gas. Other display devices, such as a panel display, can be utilized. Various controls/input devices 121 are provided for controlling the operation of the device 100.

The electrical resistance of each of the sensors 109 in the array is composed of a combination of two series resistances. First, a baseline resistance $R_b$ is present that varies across sensor design and even across sensors with the same design. This parameter depends on technology and can be considered constant regardless of the presence of gas. However, due to fabrication and aging of the device, this baseline resistance does record a variation, $\Delta R_b$. Second, another series resistance can be considered that reacts with the amount of gas it is constructed to sense, $\Delta R_{gas}$. Thus, the total resistance of a gas sensor in the array is given by Equation 1:

$$R_{sens} = R_b + \Delta R_{gas} \quad (1)$$

For the sensing elements, the sensor resistance, $R_{sen}$, ranges from 100 Ω to 20 MΩ and the baseline resistance, $R_b$, ranges from 10 kΩ to 20 MΩ. Since the system has to react to a change in resistance caused by the gas, $R_{gas}$, two different approaches are possible: keeping the current constant through the sensor and determining the voltage change due to the change in resistance, or keeping the sensor biased at a constant voltage and reading the change in current caused by the change in resistance.

In one embodiment, in order to keep the measurement as precise as possible in the given range, measures are taken to make the system insensitive to the baseline resistance, $R_b$. This is achieved according to one embodiment by incorporating a feedback loop from the digital unit to the read-out circuit to compensate for this error. Compensation of the variation of baseline resistance ($\Delta R_b$) is achieved through a signal processing independent component analysis (ICA) algorithm.

Figure 2:
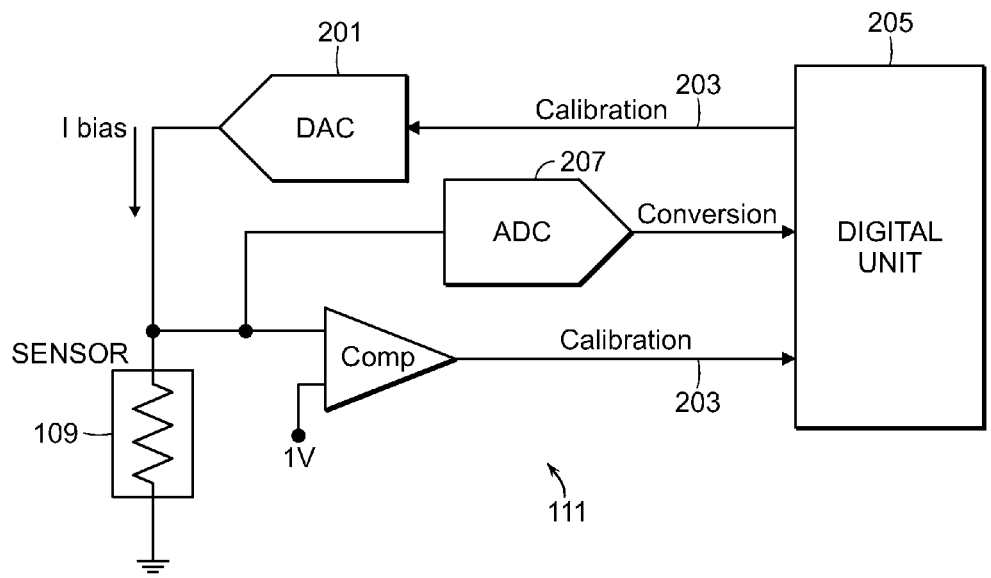
FIG. 2 is a block diagram schematically illustrating the system electronics of the diagnostic breath analyzer.

A system block diagram is shown in FIG. 2. A current D/A converter 201 is used for calibration and cancellation of the effect of inherent baseline resistance of the sensor 109. In order to calibrate for the large baseline resistance range, a feedback mechanism 203 from the digital unit 205 to the current D/A converter 201 is provided to compensate for the change in baseline resistance. Most current D/A converter topologies are either binary weighted or unary weighted. Unary current D/A converters have the advantage of inherent monotonicity, while increasing the system complexity making it unacceptable for high resolution. The binary D/A converter reduces system complexity but has the issue of monotonicity. A compromise on complexity and monotonicity is achieved and a 10 bit segmented current D/A converter topology is used with six least significant bits binary weighted and four most significant bits unary weighted.

An A/D converter 207 is then used to track the change in sensor 109 resistance with a change in gas concentration. In one embodiment, the resistance recording system requires a resolution of 16-bit and a bandwidth of up to 1 kHz. The choice of voltage-measuring first-order single-bit delta-sigma modulator matches the low-frequency content of the signal of interest, which allows high oversampling ratios and trade-off between bandwidth and resolution, and offers additional noise reduction.

In one embodiment, a temperature control system is integrated on the same mixed-signal VLSI chip, since accurate temperature control is necessary due to the strong sensor response dependence on the temperature. One or more heaters 117, such as polysilicon heaters, and temperature sensors 119 (thermometers) are included, as shown in FIG. 1, to obtain a flexible control and setting of the operating temperature gradient.

Figure 3:
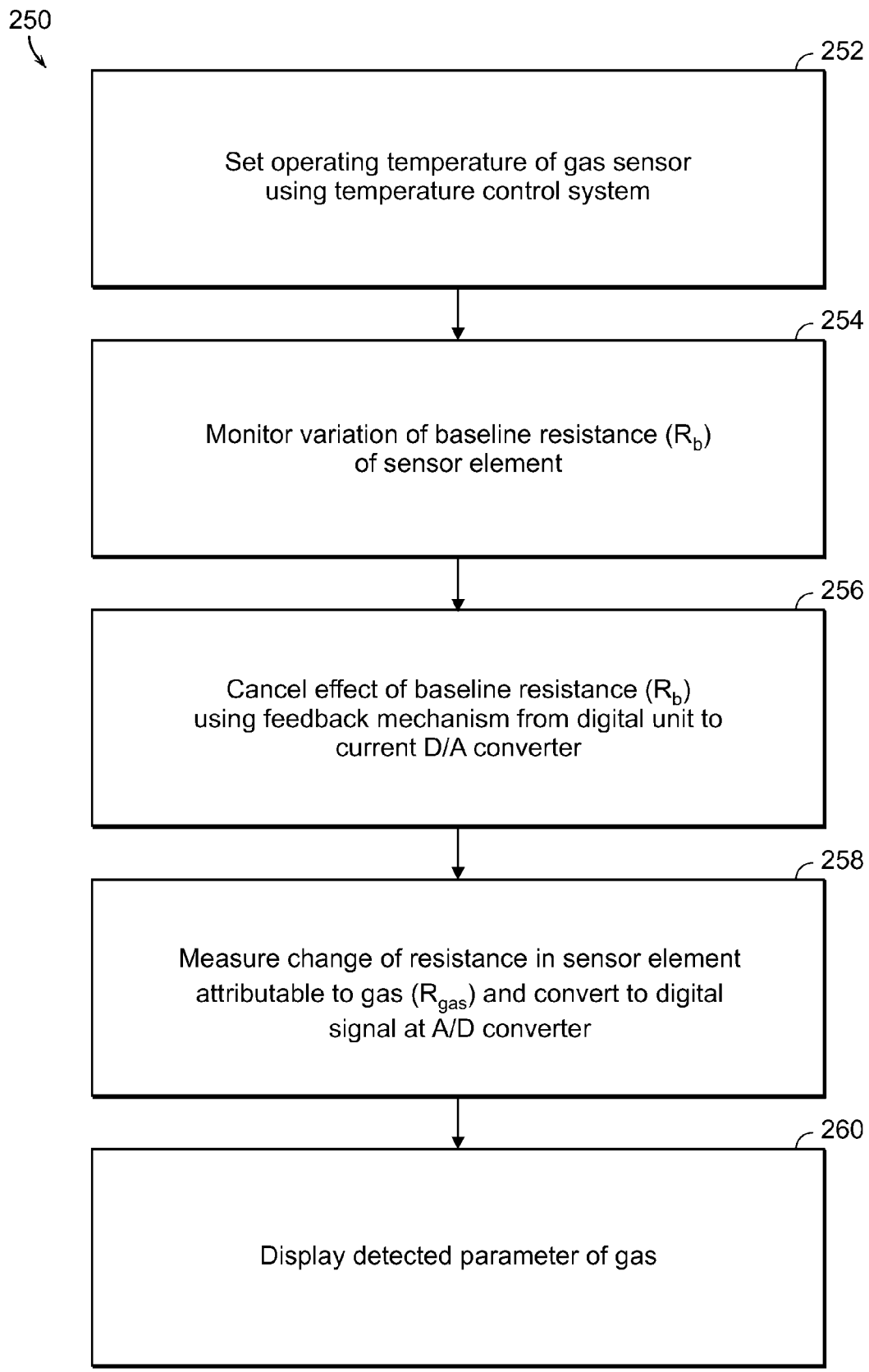
FIG. 3 is a flow diagram illustrating a gas detection method of the invention.

FIG. 3 is a flow diagram 250 illustrating a gas detection method of the invention. The method of the invention can be used to measure the concentration of a variety of substances in exhaled breath gas, including without limitation NO, NO2-, NO3-, CO, hydrocarbons, ethane, n-pentane, ethylene, isoprene, acetone, formaldehyde, ethanol, hydrogen sulfide, carbonyl sulfides, and ammonia/amines, and can further be used to diagnose a variety of diseases and medical conditions, such as inflammation and oxidative stress in the lungs, cardiovascular disease, diabetes, nephritis, bilirubin production, blood cholesterol levels, viral and bacterial infections, asthma and lung cancer. A temperature control system can be used to adjust 252 the temperature of the sensor. The method can include the steps of monitoring the baseline resistance 254, removing the effect of baseline resistance using feedback control 256, and measuring the change of resistance 258 to detect a gas parameter which is then displayed on a display 260.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A sensor for detecting gases comprising:
   a sensing element having an electrical resistance that changes in the presence of a target gas;
   a readout circuit, electrically coupled to the sensing element, that measures a change in the resistance of the sensing element due to the presence of the target gas and converts the measurement to a digital signal;
   a feedback loop from a digital unit to the readout circuit to compensate for variations in a baseline resistance of the sensing element; and
   a current D/A converter that converts a digital signal from the digital unit to a bias current that is provided to the sensing element,
   wherein the current D/A converter comprises a multi-bit segmented D/A converter having at least one binary weighted bit and at least one unary weighted bit.

2. The sensor of claim 1, wherein the sensor is incorporated in a handheld unit.

3. The sensor of claim 1, further comprising an array of sensing elements.

4. The sensor of claim 3, further comprising a multi-channel integrated readout circuit.

5. The sensor of claim 1, wherein the readout circuit comprises an A/D converter for converting the measurement to a digital signal.

6. The sensor of claim 5, wherein the A/D converter comprises a first-order single-bit delta-sigma modulator device with a digitally configurable oversampling ratio for controlling the conversion scale.

7. The sensor of claim 1, wherein the sensor maintains a constant current through the sensing element and measures a change in voltage due to the change in resistance.

8. The sensor of claim 1, wherein the sensor keeps the sensing element biased at a constant voltage and measures a change in current due the change in resistance.

9. The sensor of claim 1, wherein the least significant bit(s) are binary weighted and the most significant bit(s) are unary weighted.

10. The sensor of claim 1, wherein the readout circuit has a resolution of at least 16-bits and a bandwidth of up to 1 kHz.

11. The sensor of claim 1, further comprising a heating element and a temperature sensor for controlling an operating temperature of the sensor.

12. The sensor of claim 1, further comprising:
    a housing having an opening for receiving the exhaled breath gas of a patient, the breath gas interacting with the sensing element within the housing.

13. The sensor of claim 12, further comprising a power source incorporated in the housing.

14. The sensor of claim 12, further comprising a display device incorporated in housing.

15. The sensor of claim 1, wherein the sensing element selectively detects the concentration of a constituent of the gas comprising one or more of NO, NO2-, NO3-, CO, a hydrocarbon, ethane, n-pentane, ethylene, isoprene, acetone, formaldehyde, ethanol, hydrogen sulfide, carbonyl sulfides, ammonia, and an amine.

16. The sensor of claim 1, wherein the sensor further comprises a signal processing integrated circuit device electrically coupled to the sensing element, wherein the integrated circuit device is configured to provide a diagnosis of a medical condition including one or more of inflammation and oxidative stress in the lungs, cardiovascular disease, diabetes, nephritis, bilirubin production, blood cholesterol levels, and viral and bacterial infections.

17. A method of analyzing a gas, comprising:
    introducing a gas to a sensing element having an electrical resistance that changes in the presence of one or more constituents of the gas;
    measuring a change in the resistance of the sensing element due to the presence of the gas using a readout circuit, and converting the measurement to a digital signal; and
    compensating for variations in a baseline resistance of the sensing element using a feedback loop from a digital unit to the readout circuit,
    whereby a digital signal from the digital unit is converted to a bias current by a current D/A converter, the bias current being provided to the sensing element, and
    wherein the current D/A converter comprises a multi-bit segmented D/A converter having at least one binary weighted bit and at least one unary weighted bit.

18. The method of claim 17, further comprising providing the sensing element in a handheld unit.

19. The method of claim 18, further comprising providing a power source in the unit.

20. The method of claim 18, further comprising providing a display device in the unit.

21. The method of claim 17, further comprising providing an array of sensing elements.

22. The method of claim 21, further comprising providing a multi-channel integrated readout circuit coupled to the array of sensing elements.

23. The method of claim 17, further comprising converting the measurement to a digital signal using an A/D converter.

24. The method of claim 23, wherein the A/D converter comprises a first-order single-bit delta-sigma modulator device with a digitally configurable oversampling ratio for controlling the conversion scale.

25. The method of claim 17, further comprising maintaining a constant current through the sensing element and measuring a change in voltage due to the change in resistance.

26. The method of claim 17, further comprising biasing the sensing element at a constant voltage and measuring a change in current due the change in resistance.

27. The method of claim 17, wherein the least significant bit(s) are binary weighted and the most significant bit(s) are unary weighted.

28. The method of claim 17, wherein the readout circuit has a resolution of at least 16-bits and a bandwidth of up to 1 kHz.

29. The method of claim 17, further comprising controlling an operating temperature for the sensing element with a heating element and a temperature sensor.

30. The method of claim 17, further comprising introducing breath gas to the sensing element.

31. The method of claim 30, further comprising providing the sensing element in a housing having an opening for receiving exhaled breath gas.

32. The method of claim 17, further comprising detecting a constituent of the gas that includes one or more of NO, NO2-, NO3-, CO, a hydrocarbon, ethane, n-pentane, ethylene, isoprene, acetone, formaldehyde, ethanol, hydrogen sulfide, carbonyl sulfides, ammonia, and an amine.

33. The method of claim 17, further comprising using the digital signal from the readout circuit to indicate a diagnosis of a medical condition including one or more of inflammation and oxidative stress in the lungs, cardiovascular disease, diabetes, nephritis, bilirubin production, blood cholesterol levels, and viral and bacterial infections.

34. The method of claim 33, further comprising:
displaying the indication of a diagnosis on a display device.

* * * * *